Figure 1:
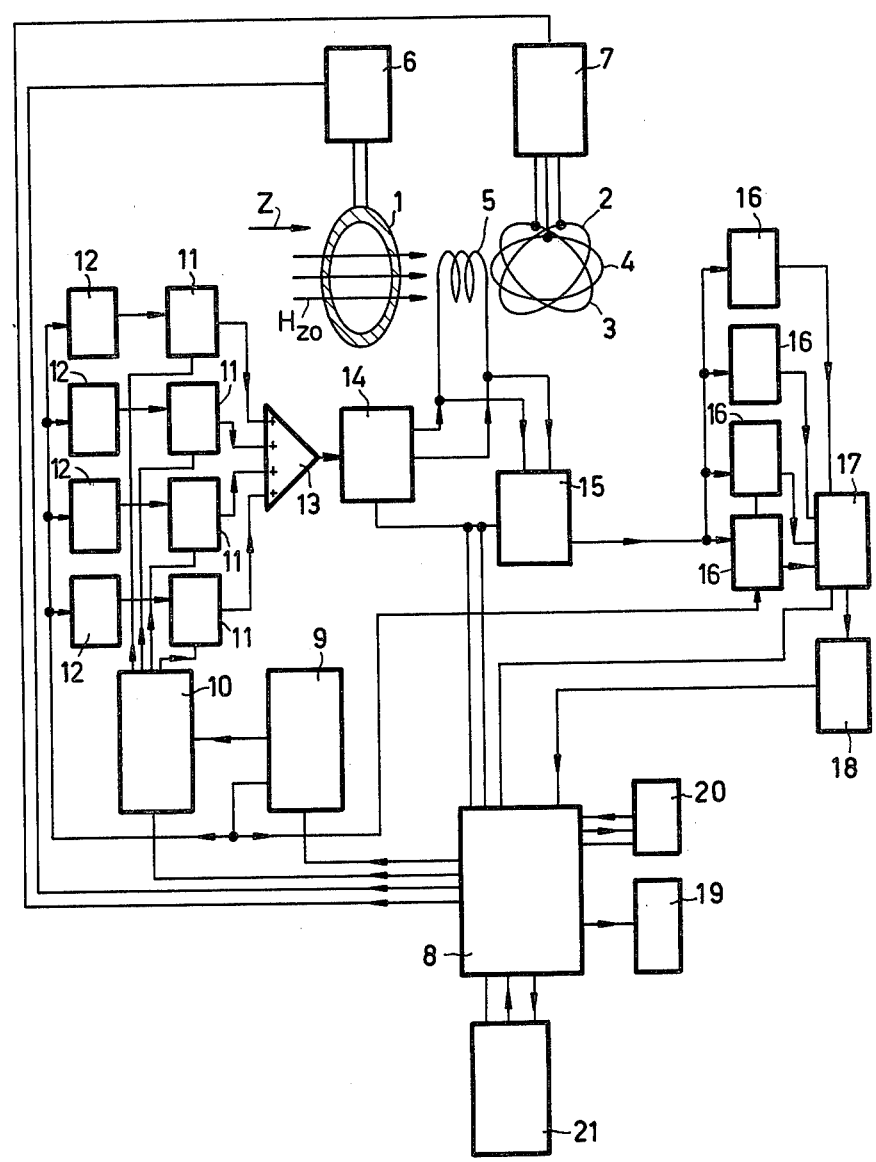

United States Patent [19]

Heinzerling

[11] 4,320,342
[45] Mar. 16, 1982

[54] MAGNET COIL ARRANGEMENT FOR GENERATING LINEAR MAGNETIC GRADIENT FIELDS

[75] Inventor: Jürgen Heinzerling, Hamburg, Fed. Rep. of Germany

[73] Assignee: U.S. Philips Corporation, New York, N.Y.

[21] Appl. No.: 75,474

[22] Filed: Sep. 14, 1979

[30] Foreign Application Priority Data

Sep. 15, 1978 [DE] Fed. Rep. of Germany ....... 2840178

[51] Int. Cl.³ .............................................. G01N 27/00
[52] U.S. Cl. .................................... 324/319; 324/320
[58] Field of Search ................................ 324/318–320

[56] References Cited

U.S. PATENT DOCUMENTS 2,265,041 12/1941 Hipple, Jr. .......................... 324/320
3,566,255 2/1971 Jaynes ................................. 324/320
3,569,823 3/1971 Golay .................................. 324/320

Primary Examiner—Michael J. Tokar
Attorney, Agent, or Firm—Jack E. Haken

[57] ABSTRACT

The invention relates to a magnet coil arrangement for generating linear magnetic gradient fields by means of which a three-dimensional spin density distribution of a body can be reconstructed (spin imaging). The magnet coil arrangement inter alia consists of a plurality of groups of single coils which are each time situated on an imaginary cylinder surface and which produce a magnetic field gradient in the interior of the cylinder which is constant over a larger range with respect to known magnetic coil arrangements. The magnetic coil arrangement also comprise four single coils which are situated on an imaginary spherical surface and wherethrough the same current flows for generating a constant field gradient which extends rotation-symmetrically with respect to an axis of examination.

4 Claims, 5 Drawing Figures

MAGNET COIL ARRANGEMENT FOR GENERATING LINEAR MAGNETIC GRADIENT FIELDS

The invention relates to a magnet coil configuration for generating linear magnetic gradient fields, in an apparatus for determining the nuclear spin density distribution of a body, consisting of at least one group of four identical rectangular coils which are situated on an imaginary cylinder surface, each time two oppositely situated coil sections thereof extending parallel to the cylinder axis, the angular distances between adjacent coil sections of each time neighbouring coils being equal in the circumferential direction of the cylinder, the same current flowing through said coils in different directions in the circumferential direction.

A cylindrical magnet coil configuration of this kind is known from the article "Nuclear magnetic resonance zeugmatography for medical imaging" by Ching-Ming Lai, Wylon V. House, Jr. and P. C. Lauterbur, Department of Chemistry, State University of New York at Stony Brook, Stony Brook, N.Y. 11794. By means of this arrangement a magnetic gradient field can be generated whose field strength is a linear function of the distance from the cylinder axis in a plane in the coil centre perpendicular to the cylinder axis along a first axis which intersects the cylinder axis, the magnetic field extending perpendicularly to the first axis. The magnetic field gradient has a constancy which is better than 1% in a central zone of the magnet coil arrangement whose radial range is smaller than one quarter of the cylinder diameter. The zone in which the constancy of the magnetic field gradient is better than 1% is thus comparatively small with respect to the radius of the magnet coil arrangement. When larger linear magnetic gradient fields are required, for example, for magnetic resonance arrangements for examining the nuclear spin density distribution of a human body, the magnet coil arrangements must be proportioned accordingly larger, so that the cost of such arrangements is increased.

The invention has for its object to provide a magnet coil arrangement for generating linear magnetic gradient fields in which the radial range of the central zone in which the constancy of the magnetic field gradient is better than 1% is substantially increased with respect to the cylinder diameter.

This object in accordance with the invention is achieved in that either the length of the coil sections extending parallel to the cylinder axis corresponds to approximately 2.9 times the cylinder radius and that the angular distances amount to approximately 30.3 degrees, or in that the length corresponds to approximately 1.1 times the cylinder radius and the angular distances amount to approximately 50.9 degrees.

The magnetic field generated inside the cylinder by the four coils arranged on the cylinder surface extends in a plane (central zone) perpendicularly to the cylinder axis in the centre of the coils, so that it increases linearly with the distance from the cylinder axis along a first axis which intersects the cylinder axis and which extends symmetrically between each time two adjacent coil sections of neighbouring coils, the magnetic field extending perpendicularly to the first axis. The magnetic field gradient formed is called a transversal gradient because the vector pointing in the direction of the largest increase of the magnetic field and the magnetic field itself extend perpendicularly with respect to each other.

As a result of the given magnet coil arrangements it is achieved that the central zone in which a constancy of the magnetic field gradient of more than 1% is required is increased to approximately 42% of the cylinder radius in the first case and to approximately 32% of the cylinder radius in the second case, so that a larger object range is covered by a linear magnetic gradient field with the same dimensions of the coil arrangement.

When images representing the internal structure of a body are made by means of the magnetic resonance method (spin imaging), individual nuclear induction signals (nuclear resonant signals or image signals) originating from different parts of the body are separated from each other by different resonant frequencies of the nuclear spins in the body. The resonant frequency is then determined by the strength of a magnetic field penetrating the body, said magnetic field consisting of a homogeneous magnetic field (Hzo) and further magnetic gradient fields with constant magnetic field gradients. Preferably, for a three-dimensional examination of the body, two mutually perpendicular magnetic field gradients extend each time perpendicularly to the direction of the homogeneous magnetic field, whilst a third magnetic field gradient extends in the direction of the homogeneous magnetic field. If a single magnetic field could be generated, having different magnetic field strengths at different areas of the body, a simple Fourier analysis of the nuclear induction signal could be used for image reconstruction. However, because the desired correlation of the location and the resonant frequency is possible only in a one-dimensional manner, or in a two-dimensional manner with restrictions, only given areas of the body can be successively excited. It follows therefrom that the magnetic field strength in the body must be variable in a defined manner. On the other hand, the variation of the magnetic field strength (homogeneous magnetic field strength plus field strength of the gradient field) over the area of the body may not be too large, because otherwise the frequency bandwidth of the nuclear induction signal becomes too large and, because of the Fourier transformation properties, the available duration of the nuclear induction signal becomes too short. Therefore, the amount of the magnetic field gradients will be chosen to be as small as possible in order to obtain a large signal-to-noise ratio of the nuclear induction signals.

In order to recover unambiguous nuclear induction signals, the magnetic field gradients, however, must be so large that the unavoidable pulsations of the magnetic field do not lead to ambiguity. The required reduced pulsation of the magnetic gradient fields or higher constancy of the corresponding field gradients, however, implies that all multipole components of higher order of the magnetic gradient fields must be very small. The total magnetic field thus contains, besides the homogeneous magnetic field (Hzo=const.), only the gradient fields which are linearly dependent of the location and whose magnitude can be adjusted (with constant magnetic field gradients). Furthermore, the constancy of the magnetic field gradients determines the resolution which can be achieved as regards the nuclear induction signals, said resolution being higher as the constancy of the magnetic field gradient and the homogeneous field is higher.

In an attractive elaboration in accordance with the invention, the magnet coil arrangement for an apparatus for determining the nuclear spin density distribution of a body comprises two groups of four coils each, each group being accommodated on an imaginary cylinder surface, the cylinder axes extending perpendicularly to each other and perpendicularly to an axis of examination which extends each time symmetrically between adjacent coil sections of neighbouring coils at half the length of the coils.

As a result of the two groups of coils, two magnetic field gradients which extend perpendicularly with respect to each other in the direction of the cylinder axes can be generated in the plane containing the two cylinder axes, said gradients being constant over a substantially larger range in relation to the radius with respect to known magnet coil arrangements. The magnetic gradient field each time generated by the coil groups extends parallel to a third examination axis which extends perpendicularly to the two cylinder axes.

Using such gradient fields, sectional images of a body containing a nuclear spin can be reconstructed in known manner, the area in which the relevant magnetic field gradients are constant being substantially larger than in known magnet coil arrangements of the same dimensions, so that larger body areas can be diagnosed.

In a further attractive elaboration in accordance with the invention, the magnet coil arrangements also comprises four flat single coils which are arranged on an imaginary spherical surface, the axis of examination extending through the centre of said single coils and perpendicularly to the planes of these coils, the single coils being symmetrically arranged with respect to the centre of the sphere which coincides with the point of intersection of the cylinder axes, the single coils wherethrough the same current flows and which comprise the same number of turns, being pair-wise arranged at pole angles of approximately 32.0 and 60.4 degrees with respect to the positive and the negative direction of the examination axis.

The single coils generate a further magnetic gradient field which extends parallel to the examination axis and rotation-symmetrically with respect thereto. The field strength is linearly dependent of the location on the examination axis. The same is applicable to field lines extending at a distance from the examination axis. Thus, the additional signel coils can generate a magnetic field gradient which extends in the direction of the further magnetic gradient field and which is constant in a zone around the centre of the sphere.

For generating a magnetic field gradient of this kind, the single coils of the known coil arrangements carry different currents, so that the ratio of the currents of the inner and the outer coil pair has a given value which has to be accurately maintained; this requires additional switching-technical steps and leads to increased costs.

The proposed arrangement of the four single coils having the same number of turns can be used to achieve that, with the same current in all single coils, the magnetic field gradient is constant in a zone whose radius corresponds to approximately 43% of the radius of the sphere.

The drawing shows an embodiment of the invention.

Figure 2A:
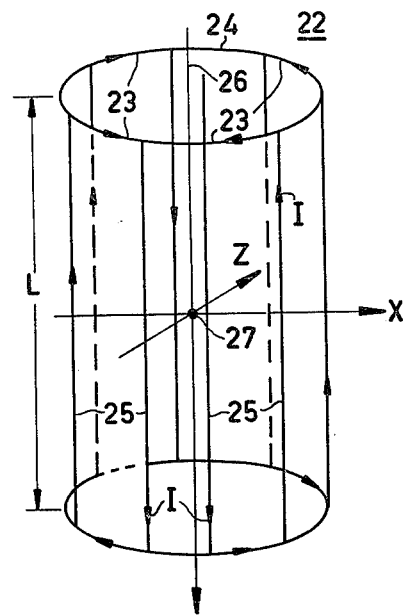
Figure 2B:
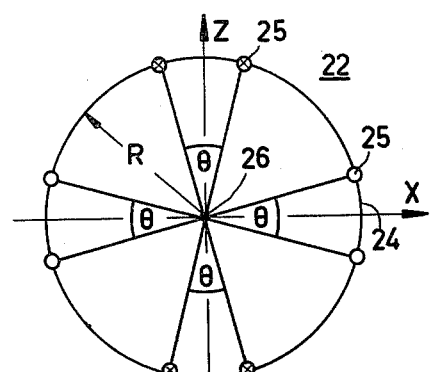
Figure 3:
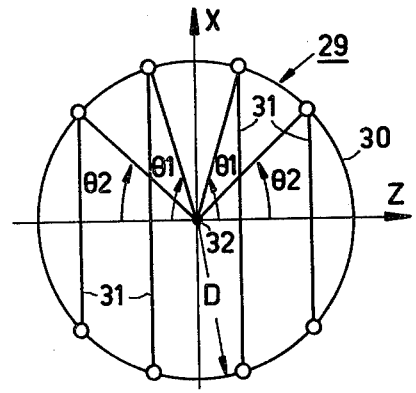
Figure 4:
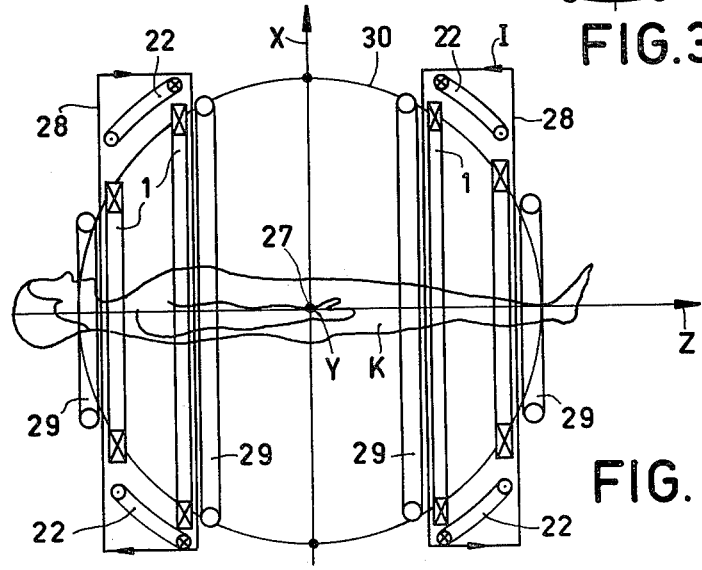

FIG. 1 is a block diagram of an apparatus for determining the nuclear spin density distribution in a body, FIG. 2a is a perspective view of a group of four coils for generating a linear magnetic gradient field, FIG. 2b is a sectional view of the group, FIG. 3 is a sectional view of single coils arranged on an imaginary spherical surface, FIG. 4 shows a magnet coil arrangement for an apparatus for determining the nuclear spin density distribution in a body.

FIG. 1 shows a block diagram of an apparatus for determining the nuclear spin density distribution of a body. Therein, a field coil 1 generates a homogeneous magnetic field Hzo which extends in the direction of a coordinate axis Z and which penetrates a body K (not shown) arranged inside the field coil 1. The body K, which is positioned, for example, on a patient table, is slidable with respect to the field coil 1 in the direction of the coordinate axis Z which represents the axis of examination. Three gradient coils 2, 3 and 4 generate sufficiently constant magnetic field gradients $\partial Hz/\partial x$, $\partial Hz/\partial y$ and $\partial Hz/\partial z$, all field gradients being separately adjustable. The excitation of the nuclear spins and the measurement of the nuclear induction (nuclear resonant) signals is realized by means of a high frequency coil 5. The gradient coils 2, 3 and 4 as well as the high frequency coil 5 enclose the body K to be examined (FIG. 4) at the area of the field coil 1. The power supply for the field coil 1 and the gradient coils 2-4 is provided by mains apparatus 6 and 7 which are controlled by an electronic unit 8 (arithmetic and control apparatus). The electronic unit 8 controls the complete measuring process and also serves for the subsequent reconstruction of the images representing the inner structure of the body K.

The high frequency signal required for excitation of the nuclear spin is derived from a frequency synthesizer 9 which, moreover, controls a pulse generator 10 required for generating a modulation signal. The pulse generator 10 determines, via the modulation signal and by means of the modulators 11, the duration and the frequency bandwidth of the high frequency signal which excites the nuclear spin and which can consist of a plurality of phase-shifted components which are generated by the phase shifter 12. In the adder 13, the phase shifted components of the high frequency signal are added. A high frequency power amplifier 14 supplies the HF energy required for excitation of the nuclear spin to the HF coil 5, the pulse power being between 0.05 and 1 kilowatt, depending on the measuring process and the dimensions of the body.

After successful excitation of the nuclear spin, the HF coil 5 receives the nuclear induction signal. It passes through a further HF amplifier 15, after which it is demodulated in the demodulators 16. An analog-to-digital converter 17 converts the demodulated nuclear induction signal into digital form. A subsequent signal averaging device 18 can improve the signal-to-noise ratio of different nulcear induction signals when the measuring cycle is repeated. Moreover, this device can also be used as a digital buffer memory.

Using the electronic unit 8, the desired body images can be generated from the nuclear induction signals in known manner, it being possible to display said images on a monitor 19 or to store these images in digital form in a disc memory 20. The complete arrangement is controlled via a data input/output unit 21.

FIG. 2a is a perspective view of a first group 22 of four rectangular coils 23 for generating a constant magnetic field gradient $\partial Hz/\partial x$ which are arranged on an imaginary cylinder surface 24. Each coil 23 comprises two straight lengthwise coil sections 25 which have a length L and which extend parallel to the cylinder axis 26. The cylinder axis 26 is at the same time the Y axis of a three dimensional, cartesian coordinate system XYZ, the origin 27 of which is situated halfway the height of the coils 23. The coordinate axes X and Z extend symmetrically between adjacent coil sections 25 of neighbouring coils 23; the same current I (arrow) flows through these coils in different directions in the circumferential direction. Using such a group of coils 23, a magnetic field gradient ∂Hz/∂x can be generated, so that the magnetic field strength Hz in the direction of the coordinate axis Z is accurately a linear function of the location coordinate x (linear gradient field). To this end, the coils 23 are arranged on the cylinder surface 24 at given annular distances θ.

FIG. 2b is a sectional view of the group 22 situated in the X-Z plane. On the imaginary cylinder surface 24, situated at a distance R from the cylinder axis 26, all coil sections 25 are situated at the same angular distances θ/2 from each time the nearest coordinate axis X or Z. In order to obtain a constant magnetic field gradient ∂Hz/∂x which is smaller than or equal to one percent in an as large as possible area in the X-Z plane (central zone), the ratio of the length L of the coils 23 and the radius R is approximately L/R=2.94. The angular distance θ/2 of the individual coil sections 25 from each time the nearest coordinate axis X or Z is then approximately 15.16 degrees (θ=30.3 degrees). For this case, the magnetic field gradient ∂Hz/∂x is constant to the required degree up to a distance of x=0.42 R from the cylinder axis 26.

When the ratio of the length L of the coils 23 and the radius R is approximately L/R is 1.14 and when the angular distances θ/2 of the individual coil sections 25 from each time the nearest coordinate axis X or Z is approximately 25.47 degrees (θ=50.94 degrees), the magnetic field gradient ∂Hz/∂x is also constant to the required degree up to a distance x=0,32 R from the cylinder axis 26. The radius R can be chosen in accordance with the desired range of the constant zone of the magnetic field gradient ∂Hz/∂x. The positions of the coil sections 25 shown given by the radius R or the angular distance θ/2, relate to the cross-sectional centres of the individual coil sections 25. Positioning errors in the angular distance of a few tenths of a degree are permissible for the coil sections 25, without the constancy of the magnetic field gradient becoming smaller than required in the given range. Similarly, a variation ΔL/L of the length L of the coils 23 of a few tenths of a percent does not adversely affect the required constancy of the magnetic field gradient in the given range.

For generating a further magnetic field gradient ∂Hz/∂y, a second group 28 (FIG. 4) of four coils 23 is provided, similar to the group 22. Its position with respect to the first group 22 is realized by rotation of the first group through 90° around the coordinate axis Z.

It is also possible to combine the magnet coil arrangement which generates two linear, transversal magnetic field gradients ∂Hz/∂x and ∂Hz/∂y with a magnetic coil 29, shown in FIG. 3, for providing a three-dimensionally variable gradient field. The magnetic gradient field produced by the magnet coil 29 extends in the direction of the coordinate axis Z and has a linear, axial-symmetrical field gradient ∂Hz/∂z. This means that ∂Hz/∂z is an approximately linear function of the location z on coordinate axis Z. This relationship is also applicable to points situated at a distance r from the coordinate axis Z. Using the three-dimensionally variable gradient field, three-dimensional spin density distributions of a body can be reconstructed, The magnet coil 29 consists of four flat single coils 31 which are arranged parallel to each other on an imaginary spherical surface 30 and which are situated perpendicularly to the coordinate axis Z and symmetrically with respect to the sphere centre 32 which coincides with the coordinate origin 27. The spherical surface 30 is situated at a distance D from the sphere centre 32.

In known magnet coils, a well-defined ratio of the currents in the inner and the outer coil pair is to be accurately adjusted and maintained for generating a linear, axial-symmetrical magnetic field gradient ∂Hz/∂z. However, it is often desirable to connect all single coils 31 one behind the other and to operate these coils with the same number of turns and with the same current. To this end, the single coils 31 are arranged on the spherical surface 30 so that the inner single coils 31 are situated at the same pole angles $\theta_1 = 60.4$ degrees with respect to the positive or the negative direction of the coordinate axis Z, whilst the outer single coils 31 are situated at the same pole angles θ/2=32 degrees with respect to the positive and the negative coordinate axis Z. The single coils 31 situated on each side of the sphere centre 32 then carry a current in the same direction, the direction of said current, however, being opposed on the two sides of the sphere centre 32.

Thus, a linear, axial symmetrical field gradient ∂Hz/∂z can be generated, the constancy of which is better than 1% up to a distance r=0.43 D from the sphere centre 32. Positioning errors in the pole angle of a few tenths of a degree are permissible, without the constancy being adversely effected in the stated range, the positioning tolerance being dependent on the desired constancy of the field gradient.

FIG. 4 shows an arrangement for determining the nuclear spin density distribution of a body K which is situated in the centre of a rectangular coordinate system XYZ. A field coil 1, being situated, for example, on the spherical surface 30, generates a static, homogeneous magnetic field Hzo which penetrates the body K parallel to the coordinate axis Z. The magnet coil arrangement 22 (first group) extending parallel to the coordinate axis Y generates a constant, transversal field gradient ∂Hz/∂x, whilst the magnet coil arrangement 28 (second group), rotated through 90° around the coordinate axis Z with respect to the magnet coil arrangement 22, generates a constant, transversal field gradient ∂Hz/∂y. Both magnet coil arrangements 22, 28 are constructed in the same way as described with reference to FIGS. 2a, b. For generating a constant axial symmetrical field gradient ∂Hz/∂z, the arrangement shown in FIG. 4 comprises a further magnet coil 29 which is also situated on the imaginary spherical surface 30, so that, for example, the body K can be examined in the manner described above.

The high frequency transmission coils and receive coils also required for determining the nuclear spin density distribution of the body K have been omitted for the sake of clarity.

The magnet coil arrangements 1, 22, 28 and 29, obviously, can be constructed to be so large that a patient to be examined can also sit or kneel inside these coils. Obviously, it is also possible to combine a plurality of groups of coils 22, 28 and 29 so that a plurality of transversal or axial-symmetrical magnet field gradients which extends perpendicular to each other can be generated as required.

What is claimed is:

1. In apparatus for generating linear magnetic gradient fields which comprises at least one group of four identical rectangular coils which are disposed in symmetric pairs around an axis (26), each coil including two lengthwise coil sections (25) which are parallel to the axis, all of the lengthwise sections being disposed at the same radial distance (R) from the axis; the improvement wherein the length (L) of the lengthwise sections is approximately 2.9 times the radial distance and the angle ($\theta$) subtended at the axis by adjacent lengthwise segments of neighboring coils is approximately 30.3°.

2. In apparatus for generating linear magnetic gradient fields which comprises at least one group of four identical rectangular coils which are disposed in symmetric pairs around an axis (26), each coil including two lengthwise coil sections (25) which are parallel to the axis, all of the lengthwise sections being disposed at the same radial distance (R) from the axis; the improvement wherein the length (L) of the lengthwise sections is approximately 1.1 times the radial distance and the angle ($\theta$) subtended at the axis by adjacent lengthwise segments of neighboring coils is approximately 50.9°.

3. The improvement of claim 1 or 2, comprising two groups of four coils each, the axis of each group being disposed perpendicular to the other and perpendicular to an examination axis which extends symmetrically between adjacent coil sections of neighboring coils at the midpoint of the lengthwise sections.

4. The improvement of claim 3 wherein the axes of the two coil groups and the examination axis intersect at a center (32) and further comprising four flat coils (31) which are symetrically disposed at equal distances from the center, each of the four flat coils having an identical number of turns and being excited with an identical electric current, the four flat coils further being symetrically disposed, pair wise, around the examination axis at pole angles ($\theta 1$, $\theta 2$,) of approximately 32.0° and 60.4°, respectively, to the examination axis.

* * * * *